United States Patent [19]

Vu et al.

[11] Patent Number: 4,820,495

[45] Date of Patent: *Apr. 11, 1989

[54] PLATE REACTORS FOR CHEMICAL SYNTHESES UNDER HIGH PRESSURE IN GASEOUS PHASE AND WITH HETEROGENEOUS CATALYSIS

[75] Inventors: Quang D. Vu, Neuilly sur Seine; Claude Pradel, Rueil-Malmaison; Jean-Paul Euzen, Dardilly; Jean-Francois Le Page, Rueil-Malmaison, all of France

[73] Assignee: Institut Francais du Petrole, Rueil-Malmaison, France

[*] Notice: The portion of the term of this patent subsequent to Aug. 18, 2004 has been disclaimed.

[21] Appl. No.: 768,780

[22] Filed: Aug. 23, 1985

Related U.S. Application Data

[62] Division of Ser. No. 555,260, Nov. 25, 1983, Pat. No. 4,544,544.

[30] Foreign Application Priority Data

Nov. 26, 1982 [FR] France .................................. 82 20026

[51] Int. Cl.⁴ ................................................ B01J 8/04
[52] U.S. Cl. .................................... 422/148; 422/193; 422/202
[58] Field of Search ................................ 165/165–167; 422/148, 197, 200–202, 192, 193

[56] References Cited

U.S. PATENT DOCUMENTS

| | | |
|---|---|---|
| 1,196,481 | 8/1916 | Reckinghausen et al. . |
| 1,200,940 | 10/1916 | Henri et al. . |
| 1,266,803 | 5/1918 | Henri et al. . |
| 2,744,813 | 5/1956 | Paul ...................... 422/200 |
| 3,127,247 | 3/1964 | Davis, Jr. ............... 422/202 |
| 3,666,423 | 5/1972 | Muenger ................ 422/200 |
| 3,679,373 | 7/1972 | VanCamp et al. ..... 422/200 |
| 3,751,232 | 8/1973 | Borre et al. . |
| 3,898,049 | 8/1975 | Burroughs et al. . |
| 4,225,562 | 9/1980 | Anderson . |
| 4,235,281 | 11/1980 | Fitch et al. ............ 165/165 |
| 4,368,779 | 1/1983 | Rojey .................... 165/165 |

FOREIGN PATENT DOCUMENTS 1118750 9/1964 United Kingdom .
1140071 3/1965 United Kingdom .

Primary Examiner—Michael S. Marcus
Attorney, Agent, or Firm—Millen & White

[57] ABSTRACT

The invention relates to a process and to an apparatus for effecting chemical syntheses in gaseous phase, under pressure, in the presence of a solid catalyst, for instance for ammonia synthesis from hydrogen and nitrogen or for the synthesis of methanol or higher homolog alcohols from hydrogen and at least one carbon oxide.

The reactor of substantially cylindrical shape contains a plurality of elongate compartments of parallelipiped shape, adjacent to each other, the adjacent walls of the compartments or the common walls of the adjacent compartments being gas-tight walls, said tight walls forming hollow plates wherein are provided channels for the flow of a fluid heat carrier flowing through said walls under a pressure substantially equal to the pressure to which are subjected the reaction gases.

4 Claims, 3 Drawing Sheets

PLATE REACTORS FOR CHEMICAL SYNTHESES UNDER HIGH PRESSURE IN GASEOUS PHASE AND WITH HETEROGENEOUS CATALYSIS

This is a division of application Ser. No. 555,260, filed Nov. 25, 1983, now, U.S. Pat. No. 4,544,544.

BACKGROUND OF THE INVENTION

This invention relates to a process and the corresponding apparatus for effecting chemical syntheses under high pressure with heterogeneous catalysis, from such gases as, for example, mixtures of hydrogen and carbon oxides or mixtures of hydrogen and nitrogen. The reaction zone is equipped with heat exchange plates and is essentially characterized in that:

The plates are connected to one another and to an external heat exchange apparatus, the assembly forming an exchange loop wherethrough flows a fluid heat carrier.

The fluid heat carrier inside the loop is subjected to a pressure substantially equal to that of the reaction gases, for example, the synthesis gases, preferably by establishing communication between the expansion chamber of the fluid heat carrier and, for example, the gas inlet into the reactor.

The plates which are plane are arranged either parallel to one another, or so as to form enclosures of parallelipiped shape.

Some of these plates may be tightly connected to the inner wall of the reactor, the assembly thus forming a deflected path wherethrough the gas is compelled to flow.

In view of their better compacity and mainly in view of the extensive mechanization which can be used during their manufacture, these plate apparatuses, during the last years, have been preferred to the tube-and-shell apparatuses in many fields of thermal exchange.

In the field of the reactors, the use of plate apparatuses remains however rare and uncommon.

Thus, there has been proposed (French Pat. No. 1 438 723) a type of reactor made of a piling of layers, some of which may contain the catalyst whereas the others determine channels for the flow of the heat-conveying agent. The different layers are separated by substantially plane plates.

This type of reactor, although of easy manufacture and of moderate price, remains however of limited use in view of its low resistance to internal pressure.

SUMMARY OF THE INVENTION

The processes of the invention have the purpose of extending the application of the plate apparatuses to the field of the high pressure synthesis reactions.

As a matter of fact, nearly all the main chemical basic products such as, for example, methanol and ammonia and manufactured under very high pressure.

In addition, under very high pressure the space is costly and the compacity of the plate exchangers constitutes a critical advantage.

BRIEF DESCRIPTION OF THE DRAWING

Reference will be made to the diagrammatical view of the figures.

DETAILED DISCUSSION OF THE INVENTION

Figure 1:
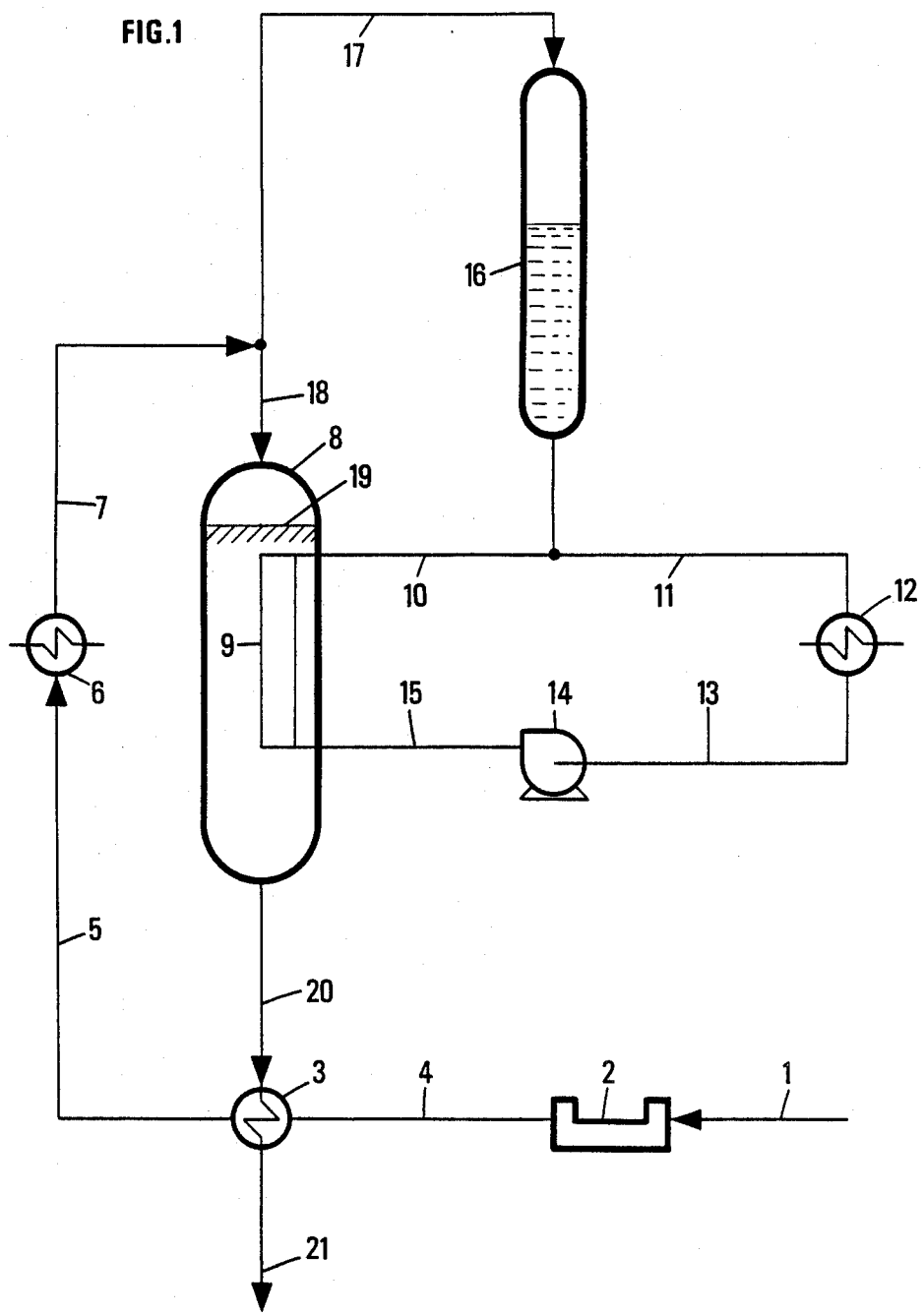
FIG. 1 illustrates conducting the process according to the present invention.

FIG. 1 illustrates conducting the process according to the present invention.

The mixture 1 of the synthesis gases, for example either hydrogen and at least one carbon oxide or hydrogen and nitrogen, is first conveniently brought to the desired pressure by means of compressor 2 and to the desired temperature by means of the exchangers between charge and effluent 3 and the reheater 6, by circulation through lines 4 and 5.

It is then introduced, through lines 7 and 18, into reactor 8, defining a cylindrical space and containing a bed 19 of solid catalyst. By contact with the catalyst, the gases react and the synthesis is effected. The reaction product is withdrawn through lines 20 and 21. The description of the reaction zone, according to the invention, is given hereinafter.

As the reaction proceeds, the temperature of the gases tends to vary as a result of the reaction heat, either evolved or absorbed. The gases are maintained under good operating conditions by thermal exchange with the heat exchange plates such as 9. These plates 9, arranged parallelly to the axis of the reactor cylinder, are connected on the one hand to one another and on the other hand to an apparatus (shown diagrammatically as 12) for heat exchange with the outside.

Fluid heat carrier destined to transfer heat from reactor 8 to exchanger 12 is caused to flow inside the plates 9 (through lines 10, 11, 13, 15) by means of pump 14.

This fluid, as a result of the thermal evolution, tends to vary in volume. These variations are made possible by the use of an expansion chamber 16 whose level variation depends on the instantaneous volume of liquid heat carrier contained in the loop formed by elements 9, 10 and 14.

The gaseous atmosphere of 16 may consist preferably of synthesis gases which have been supplied thereto through the connection pipe 17. The connection point of pipe 17 is chosen as close as possible to the inlet of reactor 8. This arrangement is thus one of those which provide for substantially the same pressure in the reaction zone and inside the plates wherethrough flows the liquid heat carrier.

As a matter of fact and as a result of this arrangement, the plates 9 are subjected to a differential pressure, which is either nil or at least negligible (0.1 to 0.5 MPa) as compared to the pressure prevailing in reactor 8, this pressure being, for example, from about 5 to 10 MPa for the methanol synthesis, or from about 20 to 100 MPa for the ammonia synthesis.

In view of this low differential pressure, the plates 9 may merely consist of two plane sheet iron plates whose spacing may be achieved, for example, by means of a web or internal structure either of corrugated sheet iron or of expanded metal, thus forming channels inside the plate, said channel giving their strength to plates which may reach or even exceed 10 meters of height, for example.

Figure 2:
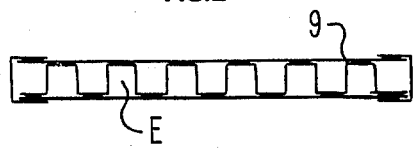
FIGS. 2, 2A and 2B respectively illustrate alternative embodiments of the sheet iron webs employed in the invention.
Figure 2A:
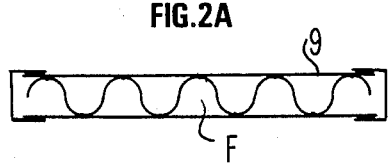
Figure 2B:
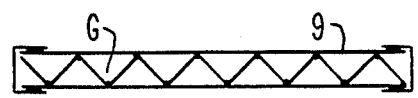

In order to impart a good turbulence to the fluid heat carrier, through the so-formed channels, the sheet iron web may have various shapes, as shown for example in FIG. 2 (channels E whose cross-section is substantially of rectangular or square shape) or in FIG. 2a (channels F whose cross-section has substantially a curvilinear, cylindrical, elliptical or circular shape) or in FIG. 2b (channels G whose section has substantially a triangular shape).

The assembling of the sheet iron elements may be effected either by welding or, much more economically, by brazing by points or by immersion into a bath, or any other convenient technique.

Figure 3:
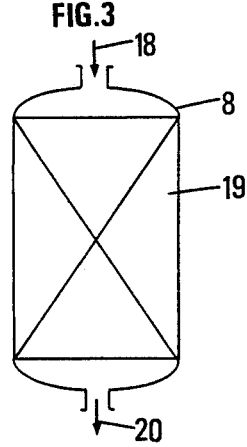
FIG. 3 shows a reactor of axial type with a catalyst bed therein.
Figure 4:
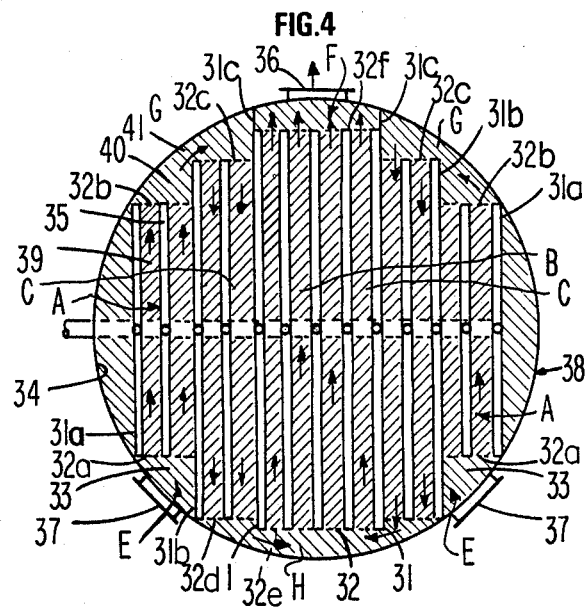
FIG. 4 is a cross-sectional view of the reactor.

In FIG. 1, as in FIG. 3, pipe 18 for the gas supply has been arbitrarily placed at the top of the reactor and pipe 20 for withdrawing the reaction effluent at the bottom of the reactor; but these pipes 18 and 20 may in fact be located at any convenient level of the reactor, as will be shown for example in FIG. 4. The catalyst supply into the reactor is effected in a conventional manner, either when fixed beds or moving beds or fluid beds or boiling beds are involved.

Generally reactors of the axial type are used.

FIG. 3 diagrammatically shows a reactor 8 of the axial type with catalyst beds 19, the inlet 18 and the outlet 20 for the reactants.

The reactor of axial type is sometimes preferred for relatively low gas flow rates (a reactor of the radial type is sometimes chosen for relatively high gas flow rates).

It is obvious that the level at which the fluid heat carrier is supplied and its withdrawing level (which in the case of FIG. 1 are respectively at the upper part for the supply and at the lower part for the withdrawal) are selected at will in upper or lower position. The arrangement of the plates, according to the invention, is illustrated in FIG. 4 and in the corresponding cross-sectional view of figure 4A.

Referring perhaps more specifically to FIGS. 5 and 5A, the catalyst is enclosed into spaces of parallelipiped shape defined by substantially parallel exchange plates 31a, 31b, 31c, etc... and permeable walls 32a, 32b, 32c etc ... These spaces are included within a circle coaxial to the circle defined by the circular section of the reaction zone.

The walls 31a and 31b form with the lower wall 34 of the reactor a connection tight to the gases introduced, through at least one line 37, into 33. Accordingly, the synthesis gases are obliged to pass through a permeable wall such as 32a before contacting the catalyst.

At the contact with the catalyst, the gases combine with each other and their temperature tends to evolve.

In order to prevent this evolution, intermediate plates 35 may be arranged in addition to the wall-forming plates 31a and 31b. The number of these plates 5 depends obviously on the heat amount involved in the reaction.

The gases flow out through permeable walls such as 32b and pass through the catalyst contained between walls 31b and 31c.

Accordingly, they pass through slots defined by walls 31b and the inner wall 34 of the reactor. This phenomenon occurs again through all the spaces of parallelipiped shape and, finally, the gases flow out through at least one opening 36 provided in the wall 4 of reactor 8.

The reactor may be described more in detail as follows (with reference to FIGS. 4 and 4a):

The cylindrical reactor 8 for chemical synthesis is subdivided into several catalyst-containing compartments 39 of parallelipiped shape.

These compartments are defined by tight walls such as 31a, 31b, 31c etc . . . which are the above-described plates wherethrough flows the fluid heat carrier and by permeable walls 32a, 32b, 32c etc . . . the latter being only shown in the cross-sectional view of FIG. 4. The permeable walls may consists either of wires in parallel or cross arrangement, or of perforated or cellular plates, or of any other equivalent type. The compartment (39) (defined by two walls 31 and two walls 32) are filled with solid catalyst, for example a catalyst for synthesizing ammonia from hydrogen and nitrogen, or for the synthesis of methanol and/or homologous alcohols from hydrogen, carbon monoxide and optionally carbon dioxide.

The fresh gases (e.g either a mixture of hydrogen and nitrogen or a mixture of hydrogen and carbon oxides) at a conveniently adjusted pressure and temperature, are introduced through at least one line 37 into the spaces 33 arranged between the cylindrical wall 34 of the reactor and the walls 31 and 32 of the catalytic compartments.

From the spaces 33, the gases pass through the permeable walls 32 for being in contact with the catalyst.

The sectional area of the compartments is so selected as to obtain a sufficient velocity of the gas through the catalyst mass. It is known that said gas velocity depends on the homogeneity of the gas distribution and on the absence of hot point at the surface of the catalyst particles.

According to the processes of the invention, the gas velocities must preferably be from 1 to 200 meters per second, preferably from 5 to 100 meters per second.

The above-indicated gas velocities are based on the gas flow rate by volume, calculated under normal conditions of pressure and temperature i.e under atmospheric pressure and at 0° C.

At the outlet of the one or more first compartments (defined by the walls 32a, 31a, 32b and 31b the gases penetrate into the void space 40 which is similar to the void space 3 at the inlet.

From a space such as 40, the gases pass through an opening (or port), such as 41, provided between the wall 31 and the wall 34 of the reactor and from there to the one or more compartments (defined by the walls 31b, 32c, 31c, 32d and so on.

In the embodiment of FIG. 4, the gas is symmetrically distributed with respect to the diameter of the reactor. It is obvious that a continuous circulation from one end to the other end of the reactor is also within the scope of the invention.

The reaction gases thus flow progressively through each of the enclosures 9 substantially perpendicularly to the axis of the reaction zone.

In all the figures the reactor is shown in vertical position but, in some cases, an oblique or even horizontal position of the reactor may be advantageous. This is, for example, the case when making use of a very elongate reactor wherein the static pressure is substantially different at the top and at the bottom.

In the case of radial reactors, this pressure difference results in an uneven distribution of the gas that different inventions have attempted to cope with (U.S. Pat. No. 3,754,078, British Pat. No. 1 118 750).

In view of the good control of the flow rate, in the case of this invention, this problem is less important. However, for a reactor of very large size, the horizontal arrangement may be of interest.

In FIG. 4, the cylindrical wall 34 of the reactor is simple and one-piece made. But, for example, in the case of ammonia synthesis, in order to avoid a decrease of the wall strength as a result of a too high temperature, the reactor wall may be lined or its strength increased by any convenient device.

When the catalyst is used under severe conditions of pressure and temperature, the problems of loading and discharging the catalyst are very important. Thus, in the reactor of FIG. 4A, the chamber 39 of parallelipiped shape may be closed at both of theirs ends so that the gases cannot pass from one chamber to another through said ends. This can be achieved by the provision of a tight plate such as 42 at each of the axial ends of said chambers (only one of these plates is shown).

One of the advantages of the process of the invention is to provide for the loading and discharge of the catalyst without disassembling the reactor and its internal parts.

Figure 4A:
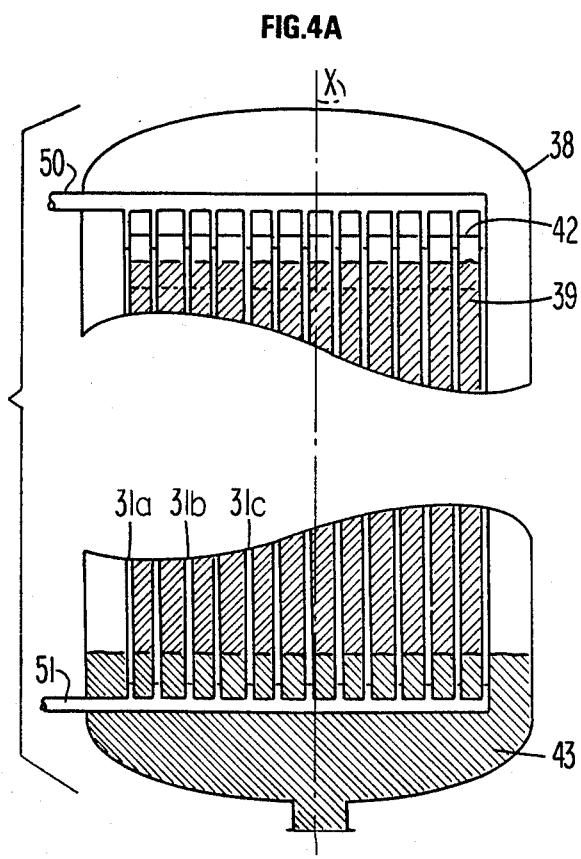
FIG. 4A is a break-away view of the reactor.

The catalyst withdrawal is particularly easy according to the embodiment shown in FIG. 4A.

In this embodiment, the bottom of the compartments of parallelipiped shape, instead of consisting of a flat bottom, is generally formed of a layer 13 of solid particles filling the generally elliptic bottom of the reactor : these particles are characterized in that their average diameter in said layer is from one half to one thousandth of the average diameter of the catalyst particles forming the catalyst bed and preferably from one fifth to one hundredth of said average diameter.

These solid particles may consist at least partially either of catalyst reduced to powder, or of metals, or of inert materials, such as alumina or carborundum or any equivalent solid.

In summary, the plurality of spaced, hollow walls 31a, 31b and 31c extend parallel to the axis X of the reaction chamber 38 and parallel to one another to define a plurality of parallel compartments 39 of which a first group A are remote from the vertical axis X, a second group B is juxtaposed with the axis X and a third group C is between first and second group. Each of the compartments 39 are further defined by first and second pervious end walls 32A, 32b, 32c, 32d, 32e and 32f which cooperate with the hollow walls 31 to retain the catalyst material in the compartments 39 and which interface with inlet plenums E, an outlet plenum F and connecting plenums G and H. The connecting plenums G and H connect first ends of compartments of the third group of compartments B with adjacent ends of the compartments of the first group of compartments A and second ends of the compartments of the third group C with adjacent ends of the compartments of the second group B. Consequently, gas under pressure introduced through the gas inlets 37 follows a sinusoidal path through the inlet plenum means E, through the first group of compartments A, into the connecting plenum means G, through the third group of compartments C, into the connecting plenum means H, through the second group of compartments B (which are adjacent the axis X; see FIG. 4), into the outlet plenum means F, and out of the gas outlet 36. While this is taking place, inlet and outlet lines 50 and 51, which are in communication with the hollow interior of the walls 31A, B and C, circulate heat transfer fluid through the walls.

In the present process, the gas charge may be introduced either at the top or at the bottom or at any point of the reactor wall, provided that said charge is subsequently distributed vertically along the permeable inlets of the catalyst enclosures.

The reactors may contain several superposed catalyst beds, each bed being accompanied with the device according to the invention.

The details of the invention as stated in the appended claims must be considered as forming part of the present description.

What is claimed as the invention is:

1. A chemical reactor having a cylindrical reaction chamber defined by a reaction chamber wall with a cylindrical inner surface formed about a central axis, the reaction chamber having catalyst material therein, the reactor comprising:

gas inlet means passing through the reaction chamber wall;

inlet plenum means within the reaction chamber and communicating with the gas inlet means; the inlet plenum means being positioned adjacent the cylindrical inner surface of the reaction chamber wall;

gas outlet means spaced from the gas inlet means and passing through the reaction chamber wall;

outlet plenum means within the reaction chamber and communicating with the gas outlet means, the outlet plenum means being positioned adjacent the inner surface of the reaction chamber wall;

a plurality of spaced, hollow walls extending parallel to the axis of the reaction chamber and being parallel to one another to define a plurality of parallel compartments of which a first group are remote from the axis, a second group is juxtaposed with the axis and a third group is between the first and second group, each of the compartments being further defined by first and second pervious end walls which cooperate with the hollow walls to retain the catalyst material in the compartments and which interface with the inlet plenum means, the outlet plenum means and connecting plenum means, which connecting plenum means connects first ends of compartments of the third group with adjacent ends of compartments of the first group and second ends of compartments of the third group with adjacent ends of the second group, wherein gas under pressure introduced through the gas inlet means follows a sinusoidal path through the inlet plenum means, through the first group of compartments, into connecting plenum means, through the third group of compartments, into other connecting plenum means, through the second group of compartments, into the outlet plenum means and out of the gas outlet means, and inlet and outlet lines in communication with the hollow walls for circulating heat transfer fluid in the hollow walls as the gas being treated by the catalyst flows through the compartments.

2. The chemical reactor of claim 1 wherein the first group of compartments comprises compartments located on opposite sides of the third group of compartments, the third group of compartments comprising a pair of groups with the second group of compartments between the pair of third groups, the inlet plenum means comprises two inlet plenums on opposite sides of the third compartments and the gas inlet includes two inlets, one connected to each inlet plenum; and wherein the outlet plenum means comprises a single plenum and the gas outlet means comprises a single outlet connected to the single plenum.

3. The chemical reactor of claim 2, wherein the inlet and outlet lines for circulating heat transfer fluid through the hollow walls are disposed above and below the hollow walls with each hollow wall being connected directly to the inlet line and to the outlet line.

4. The chemical reactor of claim 1, wherein the inlet and outlet lines for circulating heat transfer fluid through the hollow walls are disposed above and below the hollow walls with each hollow wall being connected directly to the inlet line and the outlet line.

* * * * *